United States Patent [19]
Keefer

[11] Patent Number: 5,546,818
[45] Date of Patent: Aug. 20, 1996

[54] FLUID SAMPLING APPARATUS HAVING A UNIVERSAL BASE

[75] Inventor: Richard E. Keefer, Lincoln, Nebr.

[73] Assignee: Isco, Inc., Lincoln, Nebr.

[21] Appl. No.: 444,657

[22] Filed: May 19, 1995

Related U.S. Application Data

[63] Continuation of Ser. No. 89,087, Jul. 8, 1993, abandoned.

[51] Int. Cl.⁶ ............................. G01N 1/14; F25D 3/08; B65B 3/12
[52] U.S. Cl. ............ 73/863; 73/863.83; 73/864.34; 62/457.5; 62/457.1; 220/23.83; 141/284
[58] Field of Search ................ 73/863, 863.01, 73/863.11, 863.83, 864.34; 62/457.1, 457.5; 220/23.83; 141/130, 284; 43/54.1, 55, 56

[56] References Cited

U.S. PATENT DOCUMENTS

| | | | |
|---|---|---|---|
| 2,501,772 | 3/1950 | Guard | 62/457.5 |
| 3,838,719 | 10/1974 | Lederer | 141/284 |
| 3,882,628 | 5/1975 | Stouder | 43/55 |
| 3,896,673 | 7/1975 | Audouze et al. | 73/864.34 |
| 3,924,471 | 12/1975 | Singer | 73/864.35 |
| 3,927,701 | 12/1975 | Lederer | 141/98 |
| 4,022,059 | 5/1977 | Schontzler et al. | 73/863.02 |
| 4,403,483 | 9/1983 | Lisalda | 62/457.1 |
| 4,415,011 | 11/1983 | Grant | 73/864.34 |
| 4,835,828 | 6/1989 | York et al. | 29/157.3 C |
| 4,838,239 | 6/1989 | Ordeman | 206/482 |
| 4,910,976 | 3/1990 | Drummond, III et al. | 62/457.5 |
| 5,008,084 | 4/1991 | Kelley | 220/413 |
| 5,088,618 | 2/1992 | Colombo | 220/408 |
| 5,091,863 | 2/1992 | Hungerford et al. | 73/863.01 |
| 5,405,012 | 4/1995 | Shindler et al. | 62/457.1 |

FOREIGN PATENT DOCUMENTS

| | | | |
|---|---|---|---|
| 748258 | 12/1966 | Canada | 220/413 |
| 2045281 | 12/1992 | Canada | 73/863 |
| 1503810 | 12/1967 | France | 73/863.11 |
| 2343239 | 9/1977 | France | 73/863.83 |
| 264661 | 2/1989 | Germany | 220/23.83 |

*Primary Examiner*—Hezron E. Williams
*Assistant Examiner*—Daniel S. Larkin
*Attorney, Agent, or Firm*—Vincent L. Carney

[57] ABSTRACT

A fluid sampling apparatus includes a universal base, a plurality of inner container carriers, a sequencer means, a means for holding an inner container carrier within the base, and an insulated cooler. The universal base is sufficiently large to receive any one of a plurality of different configurations of container holders or composite containers and includes locating members to properly position the different composite containers or container carriers. The container carriers include a sleeve or wall formed to have on its inner surface a plurality of indentations, each shaped and sized to receive a different one of the containers in fixed relationship to permit easy distribution of samples in the proper container.

7 Claims, 9 Drawing Sheets

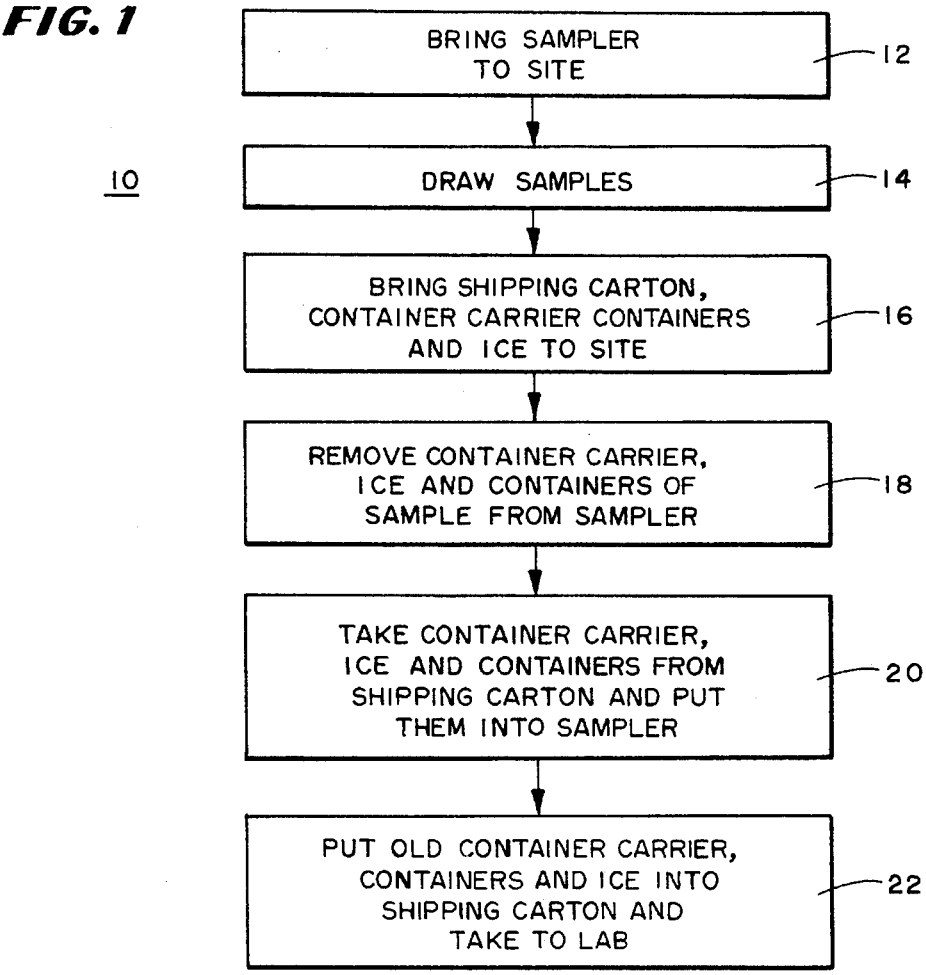
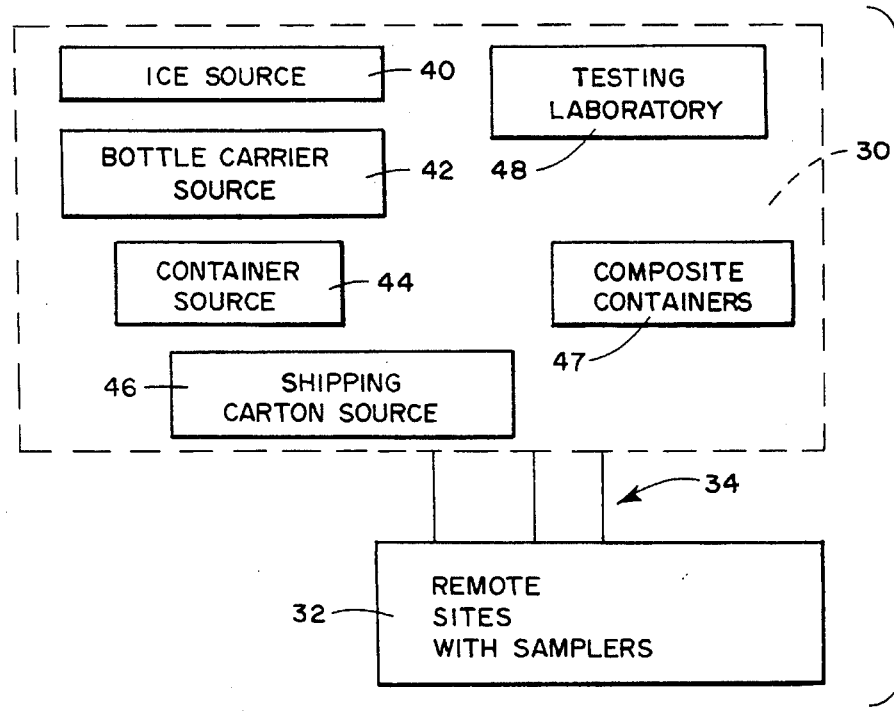

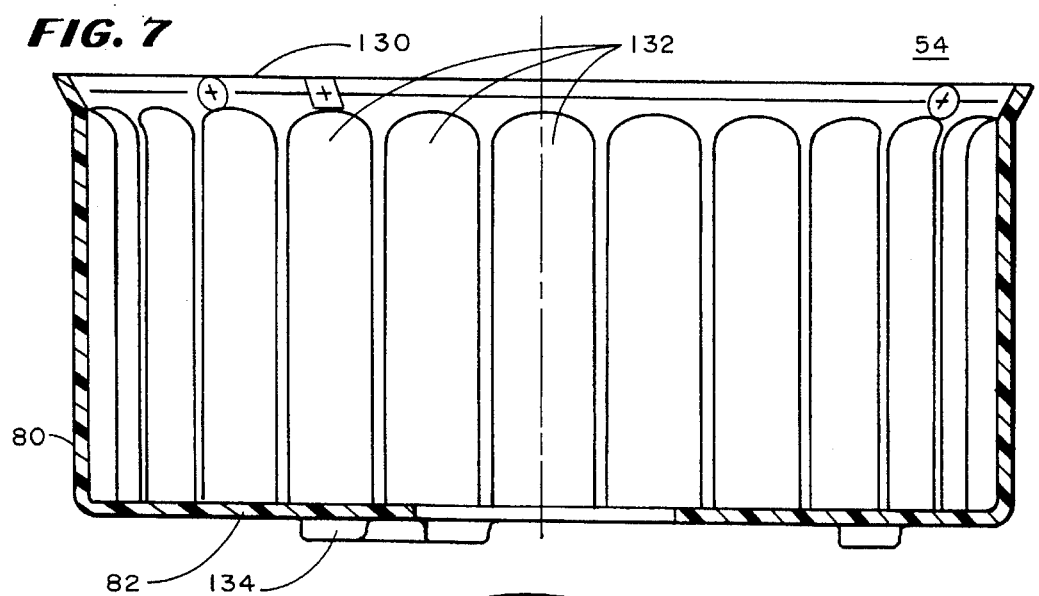
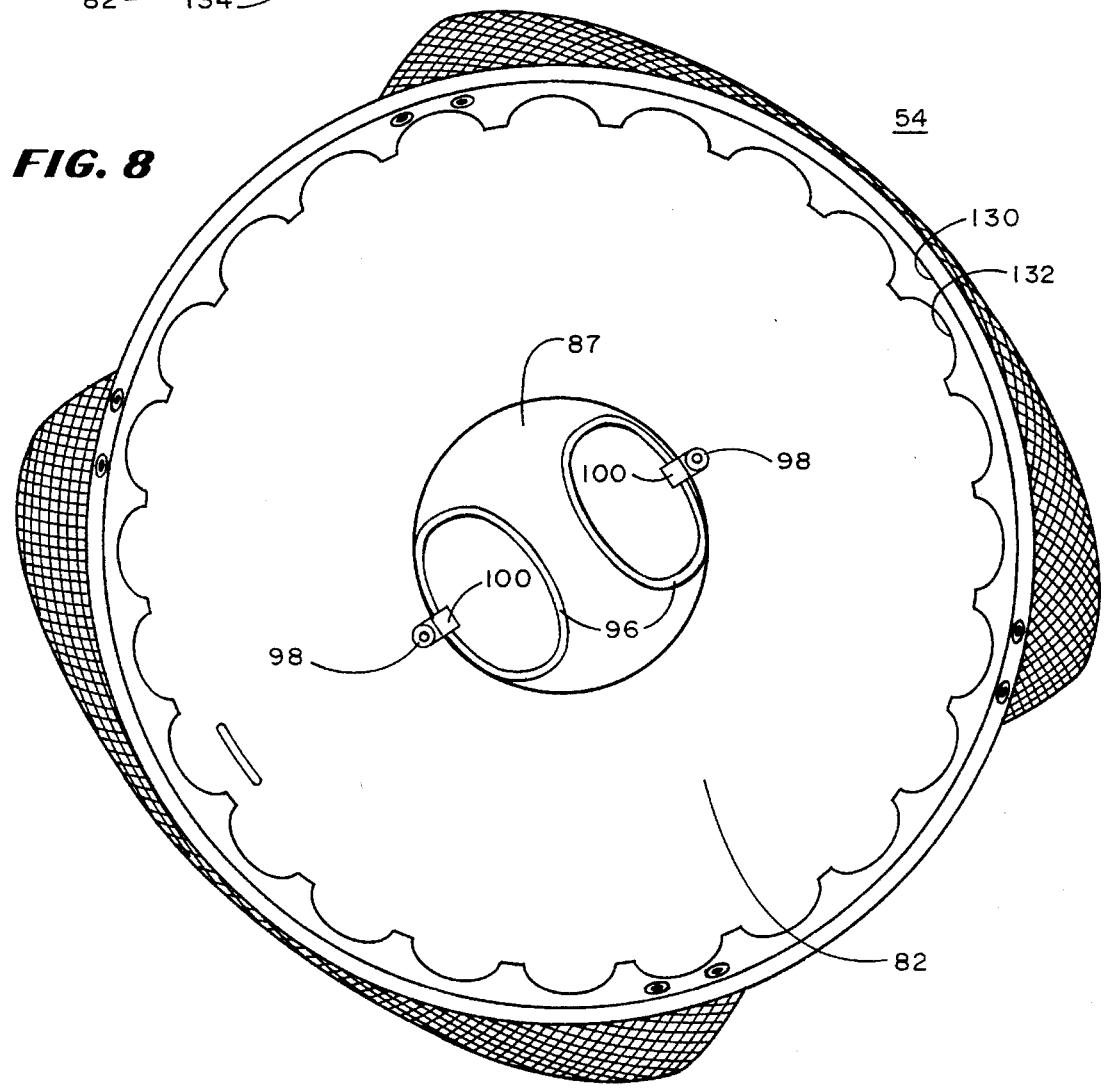

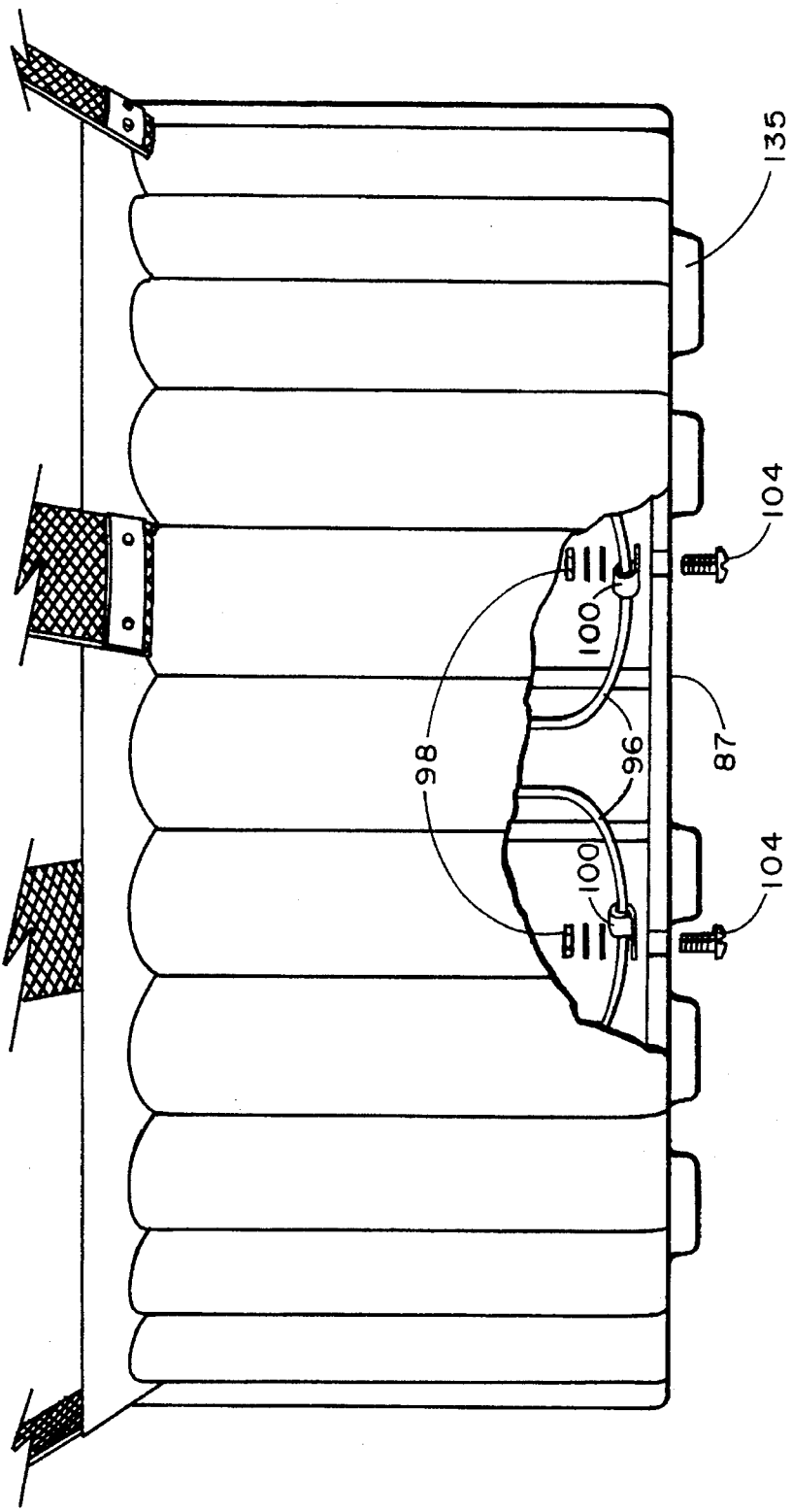

FLUID SAMPLING APPARATUS HAVING A UNIVERSAL BASE

This application is a continuation, of application Ser. No. 08/089,087, filed Jul. 8, 1993, now abandoned.

BACKGROUND OF THE INVENTION

This invention relates to methods and apparatuses for sampling fluids, such as for example, methods and apparatuses for sampling waste water from bodies of water.

In using one type of sampler, samples are automatically drawn at predetermined intervals and deposited into one or more separate containers within a housing. Generally, the housing and containers are brought from a remote location to a site for sampling, and when the samples have been drawn, they are taken to a laboratory to determine the contents of the liquid within the container or containers. Such samplers may put multiple samples taken at different times into the same container and this is called composite sampling. For other applications, samples are periodically taken such as at fixed time periods and deposited into a plurality of containers or samples are taken at intervals determined by an external device such as a flow meter that selects the time based on the amount of water that has flowed through a channel.

In this class of sampler, provision is made in a base for ice to be added. The base is adapted to receive and cooperate with a sequencer or distributor, a cover, a control module and a pump.

In one type of prior art sampler within this general class, different styles or designs of bases hold the containers, depending on whether the containers are for composite sampling or rain water run off or for other periodic sampling. In one design of such prior art samplers, a wire container holder or rack is used to carry the containers and can be inserted into a housing to hold them in place. The wire container holder is designed for the particular type of sampler to fit in its individual base.

The prior art sampling techniques and apparatuses have several disadvantages, such as: (1) a large number of base designs are required and the base designs have to be relatively heavily insulated; (2) bringing ice to cool the samples and different numbers of containers for different sampling situations requires time-consuming steps in handling the containers and the ice and the like.

SUMMARY OF THE INVENTION

Accordingly, it is an object of the invention to provide a novel sampler.

It is a further object of the invention to provide a novel technique for sampling.

It is a still further object of the invention to provide a relatively simple procedure for drawing samples even though repeated sets of containers must be used.

It is a still further object of the invention to reduce the number of parts required for several type of automatic samplers.

It is a still further object of the invention to provide a modular configuration for samplers to expedite the changing of configurations and reduce the costs of manufacturing the different configurations.

In accordance with the above and further objects of the invention, a sampler includes a universal base tub, a container carrier or inner tub, an inner sleeve and a sequencing control. It may also include a cover.

In using the sampler, after the sampler has been installed near a site and samples drawn, a new set of containers is loaded into the appropriate one of the plurality of container carriers for sampling. For example, one type of container carrier would be used for a 12-container sampling sequence and another type of container carrier for a 24-container sampling sequence. The container carrier and ice are loaded into an insulated shipping carton and brought to the sampling site. A single container for composite samples is used for some purposes, and under these circumstances, the composite container may be brought to the site in the insulated shipping carton.

At the sampling site, the old container carrier, containers with samples in them and ice are taken from the sampler and the newly brought container carrier, ice and empty containers are inserted into the universal sampler base in place of the old container carrier with containers that have had sample drawn into them. The unit is then reassembled for drawing further samples and some ice is either left in the universal sampler base or is put into the universal sampler base if all of the ice has been removed. The container carrier that has been removed from the sampler is inserted into the insulated shipping carton with the remaining ice and brought to the laboratory within the insulated shipping carton for testing of the samples.

From the above description, it can be understood that the method and apparatus for sampling of this invention has several advantages, such as for example: (1) vacuum formed container carriers may be made inexpensively and tailored for the different configurations, each of which fits with one standard insulated universal base; and (2) a convenient method and shipping carton is available for bringing the samples to a laboratory for testing.

DESCRIPTION OF THE DRAWINGS

The above noted and other features of the invention will be better understood from the following detailed description when considered in connection with the accompanying drawings, in which:

FIG. 1 is a block diagram of the steps utilized in practicing the method of this invention;

FIG. 2 is a block diagram illustrating in general the use of the novel sampler of this invention;

FIG. 7 is an elevational sectional view of the container carrier of FIG. 3;

FIG. 8 is a plan view of the container carrier of FIG. 3;

FIG. 9 is a fragmentary, elevational view, partly broken away of the container carrier of FIG. 7;

DETAILED DESCRIPTION

Figure 3:
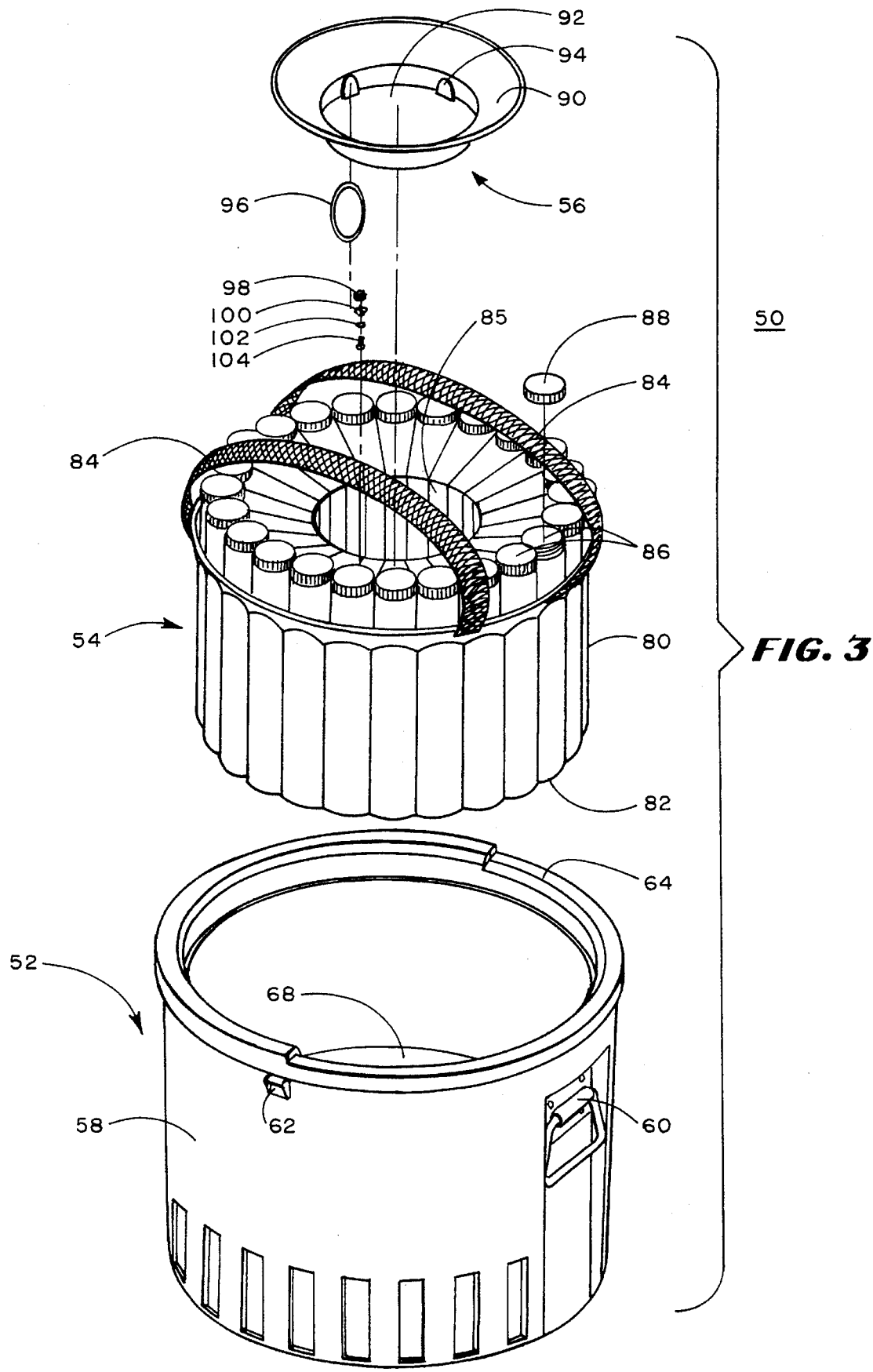
FIG. 3 is an exploded perspective view of a universal base, container carrier and container clamp down used in an embodiment of sampler.

In FIG. 1, there is shown a block diagram 10 illustrating a process of using a sampler including the step 12 of bringing the sampler to a site, the step 14 of drawing samples, the step 16 of bringing a shipping carton, container carrier, containers such as sample containers and ice to the site, the step 18 of removing the container carrier, ice and containers of sample from the sampler, the step 20 of taking the container carrier, ice and containers or bottles from the shipping carton and putting them into the sampler and the step 22 of putting the old container carrier, containers and some of the ice into the shipping carton and taking it to the laboratory.

With these steps, repeated samples may be drawn for a number of different purposes, with the only difference being the container carrier and containers that are carried to and from the site. The samples are kept cool simply and easily both during the sample taking and during the removal of the samples to a central location.

In this procedure, the sampler may be installed within a manhole or near a body of water or any other remote site and serviced for continuous sampling. The base, sequencer and cover are the same at each of the sites and for each of the purposes but the container carrier and containers may differ. They may be any of a plurality of composite containers or any of a plurality of arrangements of container carriers for carrying a plurality of individual containers and the sequencer may be programmed in accordance therewith to provide samples of any of these types.

After the samples have been drawn, a shipping carton has a replacement container carrier of the same configuration inserted into it containing empty containers. Ice is put into the shipping carton to replace the ice in the sampler that may have melted during the drawing of the samples and to keep samples being returned to the lab cool. The shipping carton is brought to the site.

At the site, the cover is removed from the sampler, the sequencer is removed and the container carrier in the sampler is removed by pulling on belts conveniently attached to it. The replacement container carrier and empty containers are removed from the shipping carton and any remaining ice in the sampler base is put into the shipping carton together with the ice that was brought. The carrier with the containers in it is inserted into the base as a replacement for the filled containers and ice is put into the base. Some of the ice is left in the carrier. The sequencer and cover are then clamped in place so as to be ready to draw a new sequence. The samples taken at the site are put into the shipping carton together with ice. It is then closed and brought to the lab for testing in accordance with step 22.

In FIG. 2 there is shown a block diagram of a sampling arrangement including a central station 30 and a plurality of remote sites illustrated at 32. The central station should include a source of ice 40, the bottle or container source 42, a source of sample containers 44 and composite containers 47 and a plurality of shipping cartons from a source 46. The samplers, periodic replacement ice, container carriers, containers and shipping cartons for the samples are moved from the central station 30 by routes 34 to each of the remote sites 32 for use and samples are moved from the remote sites in which they are taken to the laboratory which may be at the central station.

With this arrangement, different configurations of containers may be utilized with the same base at a plurality of different sites and the samples may be conveniently brought from the site to the appropriate location for the samples to be analyzed or utilized in any manner.

In FIG. 3, there is shown an exploded perspective view of a sampler bottom section 50 including a universal base 52 and a container carrier 54. The container carrier 54 includes a sleeve portion 80 with container locators and a container hold down clamp 56. It is designed to fit within the universal base 52 and be located with a specific orientation therein. The container hold down clamp 56 fits within the sleeve 80 and holds the containers in place. Fasteners hold the sleeve and hold down clamp 56 together and hold the container and the universal base securely together.

To hold different configurations of container carriers such as the 24 container holder shown at 54, the universal base 52 includes a generally cylindrical sidewall 58, a generally flat circular bottom wall 68, handles, one of which is shown at 60, a belt latch shown at 62 and a lip 64 adapted for locating a sequencer and a cover to form a closed container when desired.

The universal base is thermally insulted and has a thermal conductivity no greater than 3 BTU's per hour, per square foot in area, per inch in thickness for one degree Fahrenheit difference in temperature. It is sufficiently large to receive any one of a plurality of different configurations of container holders or composite containers as will be described hereinafter and includes locating members to properly position the different composite containers or container carriers.

In the preferred embodiment its outer diameter is 17.8 inches and it should be no greater than 18 inches nor less than 12 inches. Although the insulating material may be formed in different manners, in the preferred embodiment, the wall is hollow and contains insulating materials in a manner known in the art.

One configuration, adapted for holding 24 different containers is shown at 54 although other configurations, some of which will be discussed hereinafter may be also utilized within the same universal base 52. Generally, those configurations which are container holders containing a plurality of containers such as 12-container holders or 24-container holders have a diameter substantially in the range of 15 inches but at least a diameter that substantially conforms to the inner diameter of the base 52 although it may be smaller in diameter but not larger.

The container carrier 54 includes a locator wall or sleeve 80, a bottom portion 82, one or more belts such as the one shown at 84 and the hold down clamp 56. It is adapted to hold a plurality of containers such as the containers 86, each of which may be adapted to receive a different one of a plurality of caps 88 to close the containers after they are filled. An opening is provided such as shown at 85 which is sized to receive ice.

The sleeve or wall 80 is formed to have on its inner surface a plurality of indentations, each shaped and sized to receive a different one of the containers 86 in fixed relationship to permit easy distribution of samples in the proper container. In the preferred embodiment a radially, upwardly and outwardly extending lip cooperates with a mating surface on the lip 64 of the universal base 52 and is adapted to receive the belts such as 84 which permit the container carrier to be easily inserted within the universal base or pulled from the universal base.

The container holddown clamp 56 is generally cylindrical containing an open portion 92 through which ice may be received with a plurality of tabs such as the tab 94 around a cylindrical downwardly extending flange 90 to receive holddown fasteners in a manner to be described hereinafter. A cylindrical rim overlies a portion of the containers 86 in the preferred embodiment to aid in firmly holding the clamp in place to firmly mount the containers in place. The container carrier is fastened to the bottom 68 of the universal base 52 in a manner to be described hereinafter and the clampdown member 56 is held by O rings, one of which is shown at 96 to the bottom 82 of the container carrier 54 so that it may be moved therewith when the carrier is released from the base.

With this mechanism, the containers may be held in place as the container is moved from location to location. The O ring 96 is elastomeric to some extent and has an upper edge which fits over a corresponding one of the tabs at 94 and extends downwardly to a fastening member 100 held in place to the carrier by the fasteners 98 and 104.

With this arrangement, the clampdown member 56 may be fastened to the container carrier 54 with the containers in place and lowered into the base 52. It may then be fastened to the base properly located by locating members and held in place by other similar fasteners to be described hereinafter.

Figure 4:
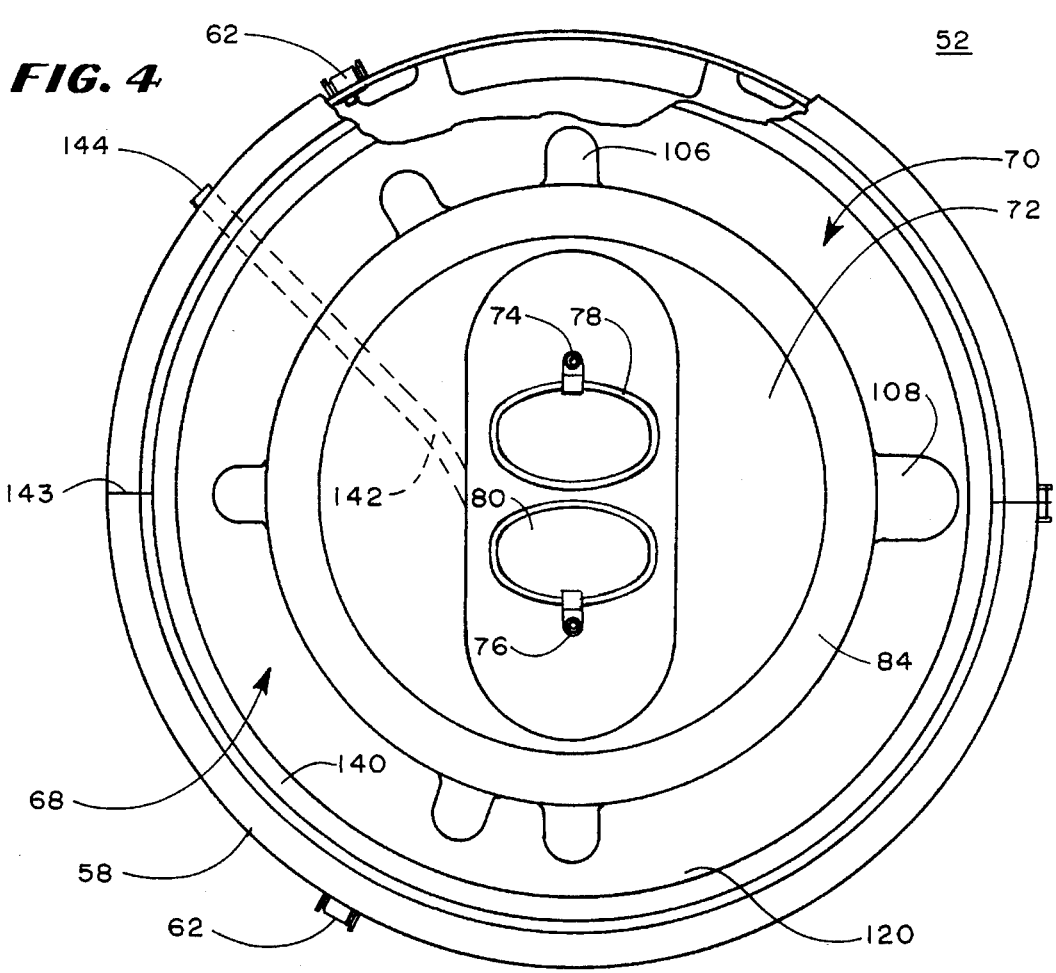
FIG. 4 is a plan view of a universal base in accordance with the embodiment of FIG. 3.

In FIG. 4, there is shown a plan view of the base 52 looking downwardly from its open end showing the outer wall 58, with the clasps 62 spaced there around and indentations on the bottom surface 68 such as for example a bottom indentation 72 sized to receive a composite container and upwardly from it an indentation 84 not as low as the indentation 72 but larger to receive another size composite sample container and finally a top layer 120 having positioning indentations to receive and locate two different sizes of container carriers. Each of these levels is adapted to receive a different container.

To permit the proper positioning of container carriers such as that shown at 54 in FIG. 3 to permit the automatic distribution of liquid into the containers within them by a distributor, each of the different containers includes a plurality of downwardly extending feet to be described hereinafter which fit in selected ones of indentations 106 or 108. The indentations are spaced so that when the container carrier is seated, the containers are aligned in accordance with a program in the sequencer to follow a predetermined order of filling the containers. In the bottom indentation 72 are a plurality of fasteners such as 74 and 76 fastened to the bottom of the base and connected to O rings 78 and 80 which may be pulled upwardly to connect with the container carriers such as the container carrier 54 (FIG. 3).

With this arrangement, containers for collecting composite samples, which containers have a central opening to receive a sample, may be seated in different ones of the layers 72 or 84 depending on the size and shape of the container bottom and one of the larger container carriers such as the carrier 54 (FIG. 3) may be seated in place on the top level 120, and when accurately located, drop downwardly as the feet extending from its bottom drop into the locators such as 106 and 108 that are spaced appropriately to only receive the proper container carrier and to position the containers in the proper programmed orientation so as to simplify programming of the distributor.

With this arrangement, a plurality of different container carriers carrying containers such as 12-container carriers or 24-container carriers in a plurality of composite holders can fit within the same base with ice and be thermally insulated. This permits a single universal base to be utilized regardless of which a plurality of types of sampling that the user wishes to undertake.

Figure 5:
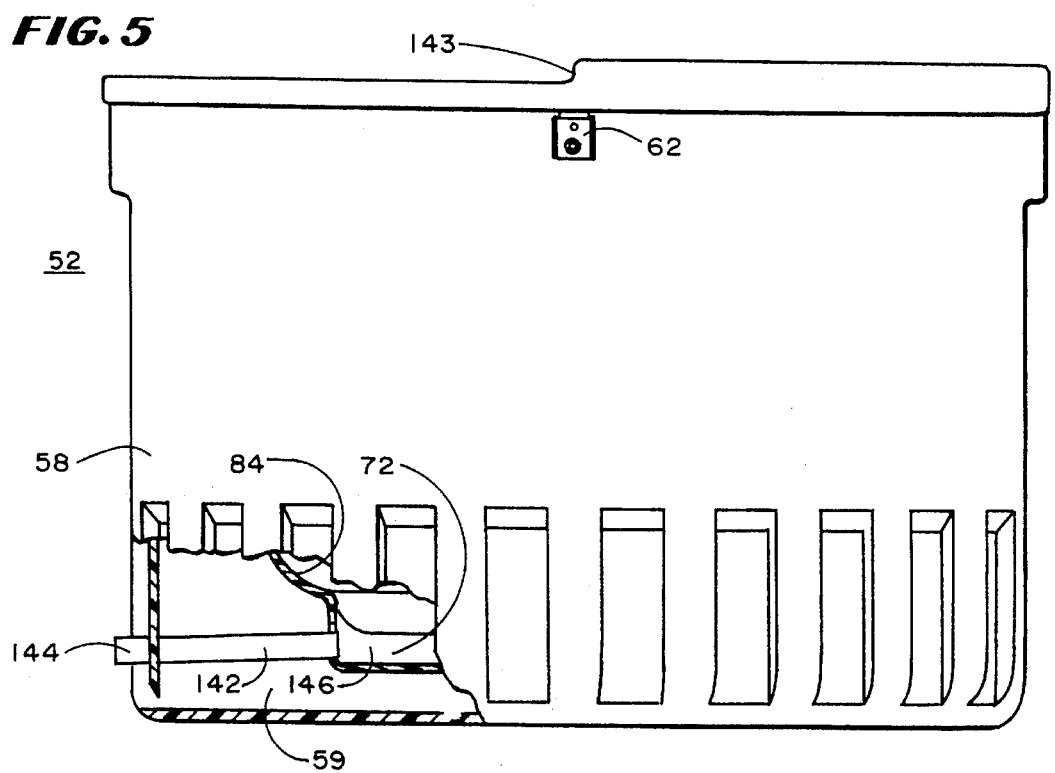
FIG. 5 is an elevational view of the base of FIG. 4.

In FIG. 5, there is shown a partly broken-away, partly sectioned, elevational view of the universal base 52 with the wall 58 broken away at 59 to show a spout 142 with a nozzle 144 adapted to communicate with the interior of the base at a low point 146 of the bottom of the base. This spout may receive water from melted ice and cause it to flow from the lowest indentation 72 outwardly from the lower base. In the upper lip, are shoulders 143 adapted to align with the sequencer and with the cover.

Figure 6:
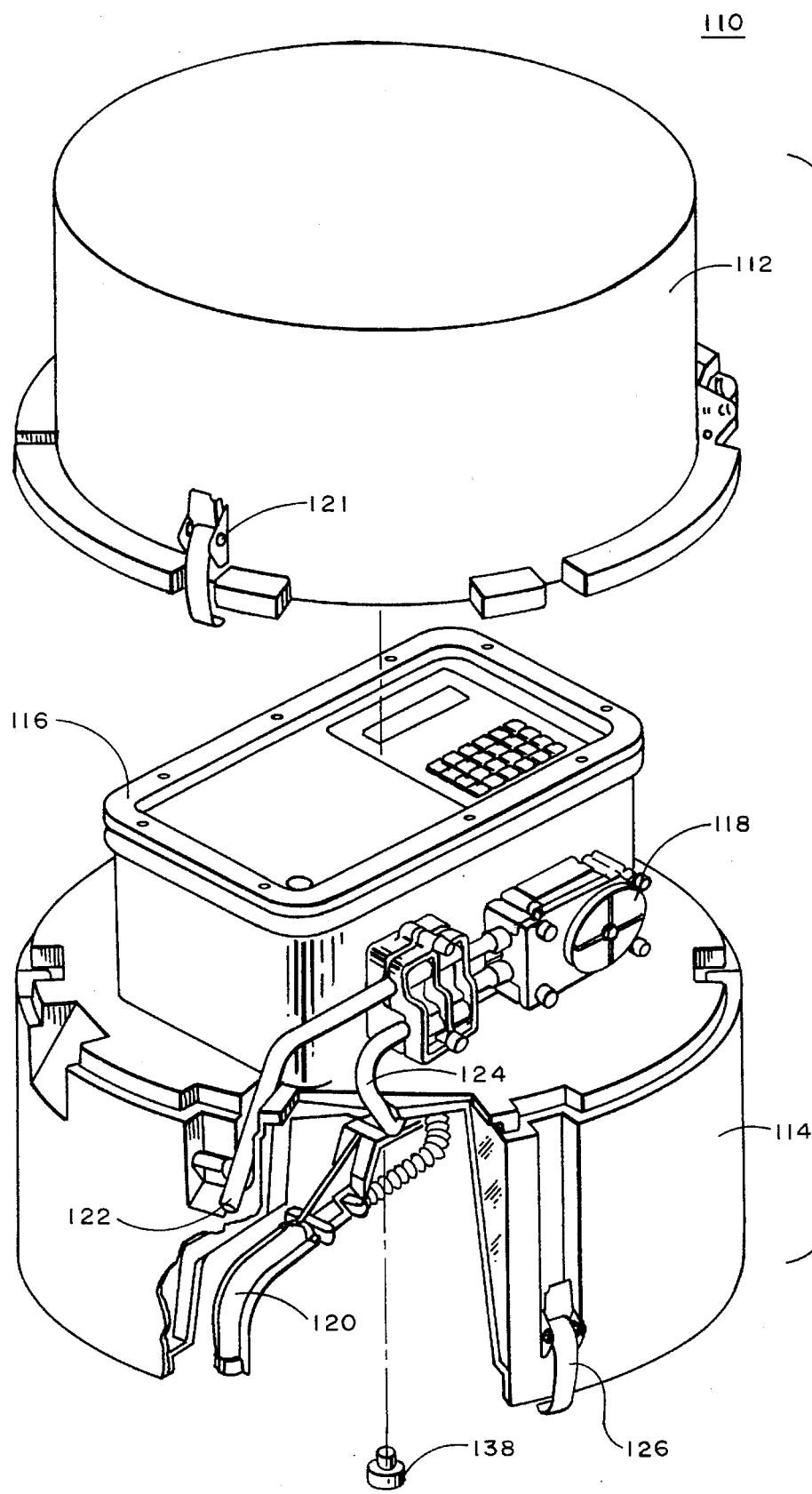
FIG. 6 is an exploded perspective view of a sequencing portion and cover for the embodiment of sampler of FIG. 3.

In FIG. 6, there is shown an exploded perspective view of a top portion 110 of a sequencer having a cover 112, a wall portion 114 supporting a control module 116 and a peristaltic pump 118 having inlet tubing 122 and outlet tubing 124 leading to a distributor 120. Clamping members such as 121 are adapted to engage with the belt latch 62 (FIGS. 3, 4 and 5) to hold the computer and distributor module in place. Similarly, clamping members 121 on the cover 112 are adapted to mount to and hold the cover to the wall 114 containing the control module 116 and peristaltic pump 118.

Similar samplers with similar pumps, covers and control modules, and distributors but without the universal base, container carriers, and shipping cartons are generally available. One such pump is sold by Isco, Inc. Environmental Division, 531 Westgate Blvd. Lincoln, Nebr. 68528-1586, U.S.A. under the designation model 3700 automatic sampler. Although there are minor modifications in the cover and computer module of the commercial unit in which the universal base and container carriers are to be included, they are not part of this invention and the general configuration has been in the prior art by use and sale. The programming sequence, however, is adapted for the particular carrier and the clamps are adapted to cooperate with the universal base in the manner described rather than in prior art configurations. The programming sequence is described more completely in the preferred embodiment in U.S. Pat. No. 5,125,801, the disclosure of which is incorporated herein by reference.

The distributor 120 is mounted in place to the wall 114 by a nut 138 to permit its nozzle to orbit about a center when liquid is to be distributed to a circular ring of containers and to permit removal of the distributor so that liquid flows directly downwardly into a center opening in a composite container when composite sampling is desired.

In FIG. 7, there is shown an elevational sectional view of the container holder 54 having a radial lip 130, a plurality of spaced-apart concave-inwardly curved sections 132, and a plurality of downwardly extending feet 134 extending from the bottom portion 82. The lip 130 is adapted to engage an upper portion of the lip of the universal base 52 (FIG. 3) and rests thereon with its wall 80 extending downwardly cylindrically inside the inner wall of the universal base.

A plurality of vertically-elongated spaced-apart radially-outwardly-concave sections 132 are adapted to receive complementarily formed concave outwardly shaped containers 86 (FIG. 3) with their side by sides wedge shaped members extending to a location near the center where they terminate to leave a cylindrical opening 85 (FIG. 3). These members thus precisely locate the containers 86, one with respect to the other, so that, when the container carrier 54, is accurately located within the base 52, the distributor deposits samples directly over the openings in each container, which openings in the preferred embodiment form a circle.

The feet 134 which extend generally as cylinders downwardly from the bottom wall 82 are shaped to fit into the appropriate bottom recesses 106 and 108 (FIG. 4) within the bottom of the base 52 and one foot 135 is of larger size to fit in one recess 108 which is larger than the other recess 106 so that the container carrier 54 may be aligned accurately be means of those feet members which serve as locators.

In FIG. 8, there is shown a plan view of the container carrier 54 having the O rings 96 fastened to the bottom of the carrier by eyelets 100 held in place by bolts, a nut of which is shown at 98. These are the O 96 rings that extend upwardly as shown in FIG. 3 to grasp tabs 94 (FIG. 3) in the container holddown clamp 56 (FIG. 3) to hold the clampdown member and the containers in place. Thus, the containers are held to the carrier by the clampdown member in a manner independent of the fastening of the carrier to the bottom of the base by other O rings 78 and 80 (FIG. 4).

With this arrangement, the O rings 78 and 80 may be released to release the carrier from the base independently of the release of the clampdown member from the carrier sleeve. Thus, the container carrier and the container clampdown may be lifted from the universal base 52 as a unit with the containers still in place. The central opening 87 which is aligned with the opening 85 (FIG. 3) permits the insertion of ice all the way down to the bottom of the container and permits liquid to drain off into the lowermost portion of the universal base 52 where it may be released by the spout 142 (FIG. 5).

In FIG. 9, there is shown an elevational view of the container carrier 54 partly broken away to show the O rings 96 attached by the bolts 104 through openings or holes in the bottom of the container carrier to permit them to extend upwardly. The opening 87 similarly allows O rings fastened to the bottom of the base 52 (FIG. 3) to extend upwardly.

Figure 10:
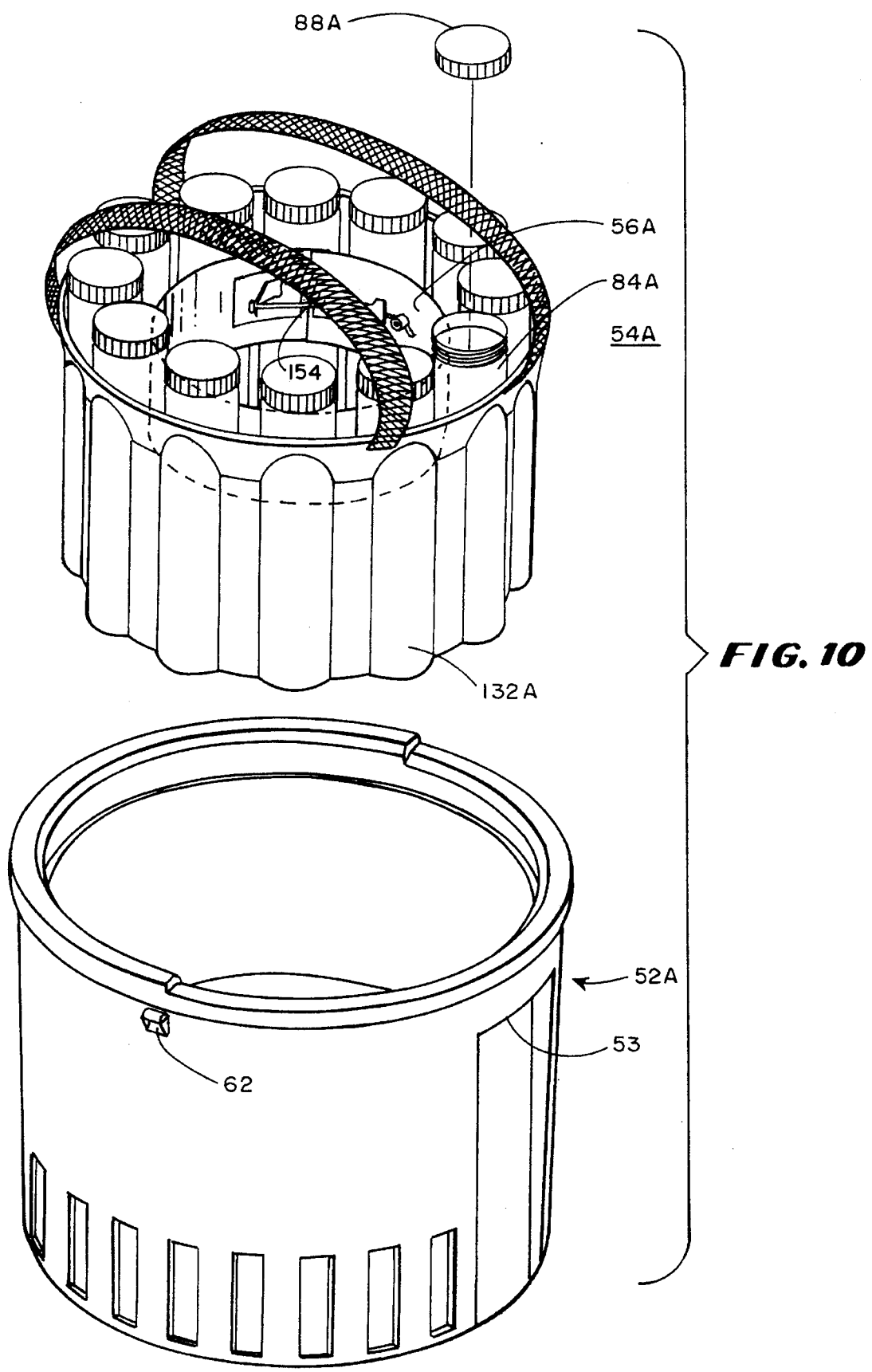
FIG. 10 is an exploded perspective view of another embodiment of universal base and another embodiment of container holder similar to the universal base and container holder of FIG. 3.

In FIG. 10, there is shown another embodiment of base 52A similar to the base 52 except that instead of hinged handles it includes molded in place handles 53 which can be gripped to lift the sampler. Similarly, a carrier 54A and container holddown clamp 56A similar to the container carrier 54 and clamp holddown 56 of the embodiment of FIG. 3. The base 52A is interchangeable with the base 52 and the carrier 54A and clamp 56A may be utilized in the universal base 52 as well as in the universal base 52A. The container carrier 54A includes spaced apart concave outwardly members 132A adapted to hold containers 84A with caps 88A. Thus the container holder 54A is adapted to hold 12 containers rather than 24 but otherwise is substantially the same as the container 54 and has the same size outer periphery to fit within the same universal base. However, the clamping member 56A, is a slightly different configuration having a split cylinder that fits within the opening 85 and presses outwardly against the containers, being biased outwardly by a biasing spring 154. It may be held in place in the same manner as the clamping member 56 and include a upward lip to engage the containers and hold them downwardly.

Figure 11:
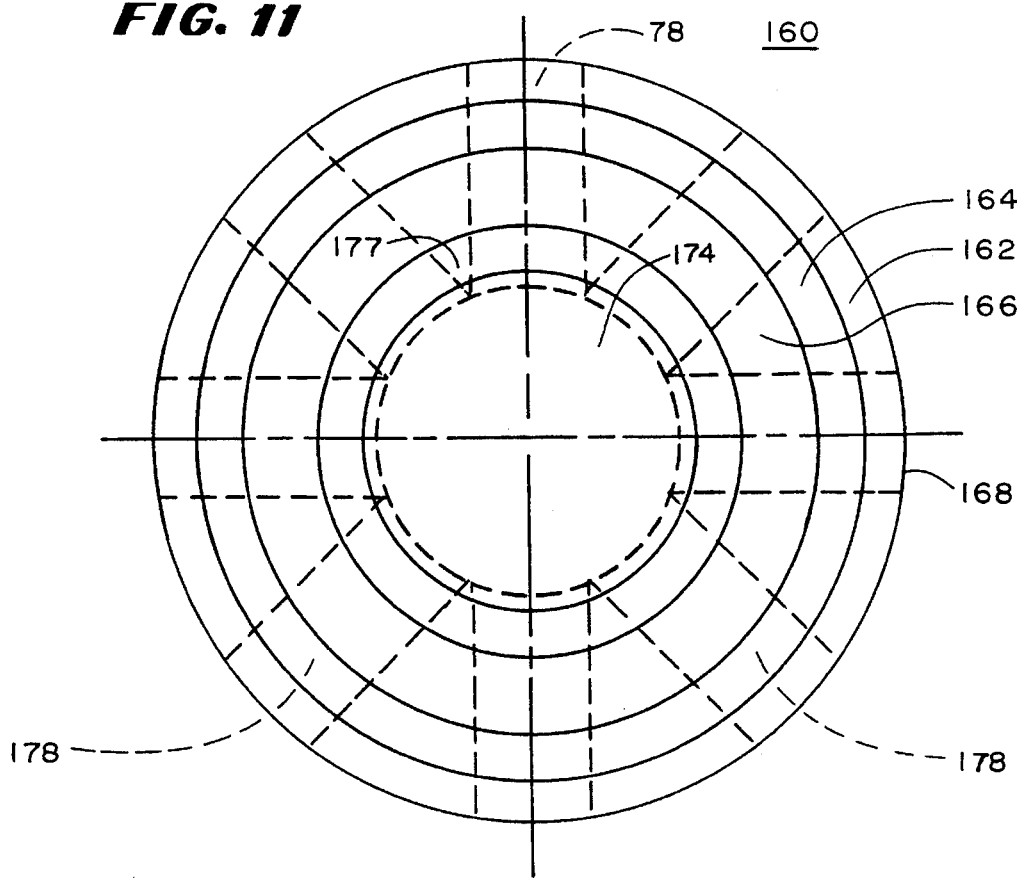
FIG. 11 is a plan view of a bottom portion of a shipping carton.
Figure 12:
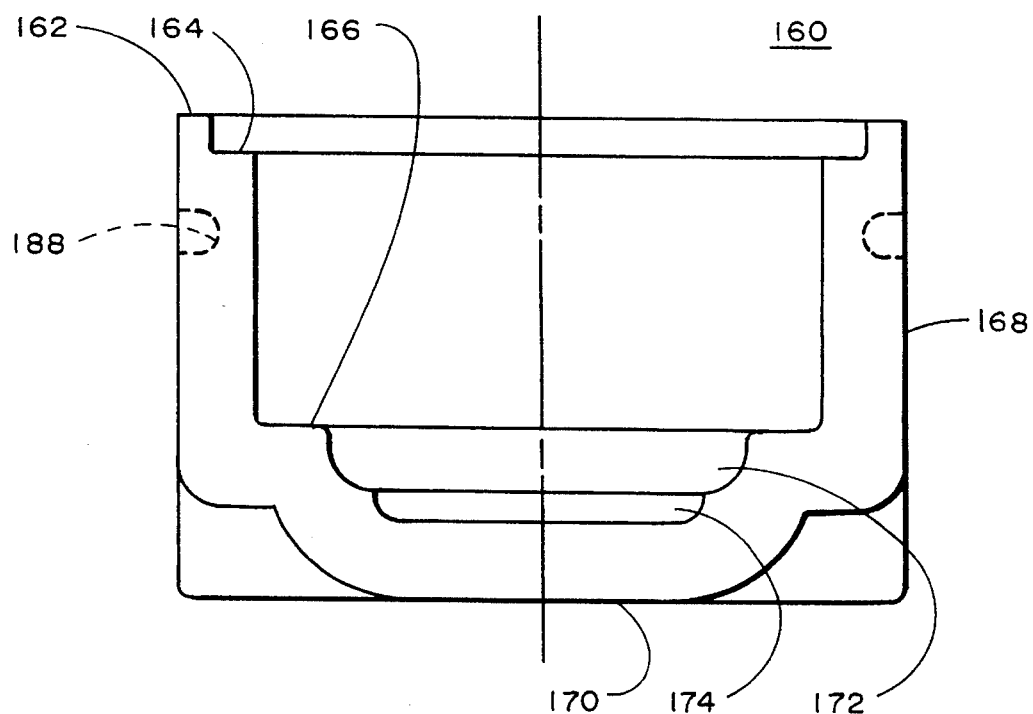
FIG. 12 is a sectional view of the shipping carton of FIG. 11.

In FIG. 11, there is shown a top view of the bottom 160 of a shipping carton having an upper rim 162, a radially inwardly lower rim 164, a first bottom ledge 166, all of with are annular and tubular cylinders, with the upward outer rim 162 forming a flat vertical downwardly surface 168 to a flat bottom surface 170 (FIG. 12). The ledge 166 is relatively low and adapted to receive container carriers such as the container carrier 54 (FIG. 3) and 54A (FIG. 10). Central to the ledge 166, is a curved downwardly extending recess 172 (FIG. 12) and a still smaller radial recess 174, (FIG. 12) each of which are adapted to receive different ones of composite containers 47 (FIG. 2) in a manner similar to the universal base 52 (FIG. 4). A plurality of undercut portions 178 in the bottom elevate portions of the bottom, expedite molding and reduce the amount of material needed.

Figure 13:
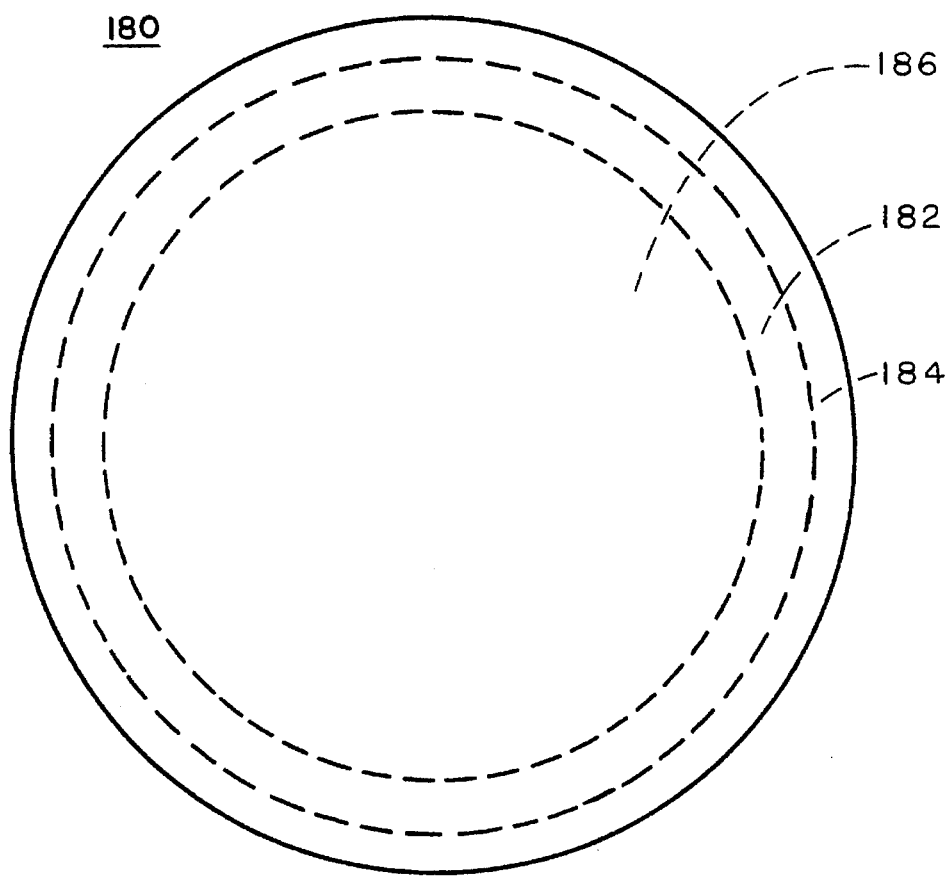
FIG. 13 is a plan view of a top portion of the shipping carton of FIG. 11.
Figure 14:
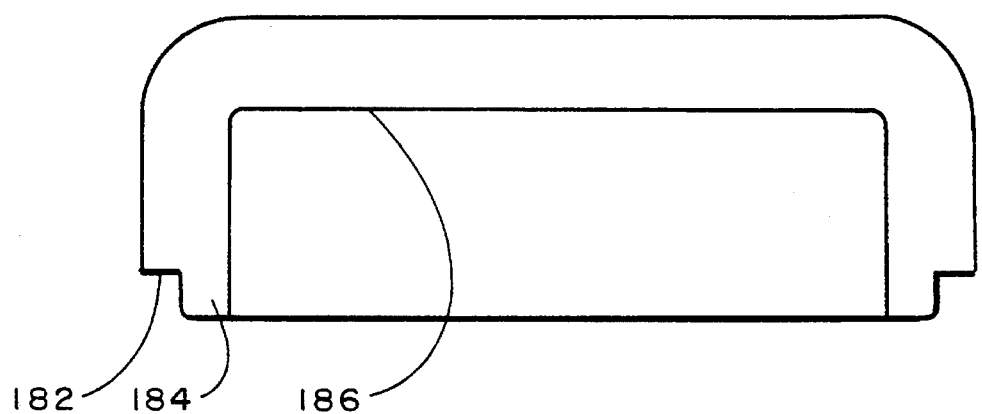
FIG. 14 is a sectional elevational view of the top portion of the shipping case of FIG. 13.

In FIGS. 13 and 14, there is shown a top portion of the casing or cooler 180 of a shipping carton adapted to cooperate with the bottom portion 160 (FIG. 11) and having for that purpose a radially outwardly recessed ledge 182, an elevated radially inwardly tubular ledge 184 and a recess 186 adapted to form an insulative top portion which can be readily seated in place. Along the sides of the bottom, are undercut handles shown in FIG. 12 at 188 for conveniently lifting and carrying the cooler.

The cooler is molded from styrofoam in the preferred embodiment but may be made of any material. Preferably, it should be insulated so as to be suitable for carrying cooled samples to the laboratory and carrying ice out to remote samples.

From the above description, it can be understood that, the method and apparatus for sampling of this invention has several advantages, such as for example: (1) it is inexpensive to manufacture; (2) it is simple to use and can conserve time; (3) it requires fewer parts for handling different configurations of containers and different sampling techniques.

Although a preferred embodiment of the invention has been described with some particularity, many modifications and variations of the invention are possible within the light of the above teachings. Therefore, it is to be understood, that, within the scope of the appended claims, the invention may be practiced other than as specifically described.

What is claimed is:

1. A sampler comprising:

a base;

said base having an outer surface, an inner surface and a top portion;

a plurality of inner container carriers;

said inner surface having locating members therein adapted to cooperate with mating surfaces on said inner container carriers;

each of said inner container carriers having one of a plurality of configurations, each of which has a shape and size that permits it to fit within said inner surface and match with said locating members, whereby different configurations of inner container carriers can fit with different orientations within said base, whereby a plurality of different inner container carriers containing different arrangements of containers can be inserted in the same base; and sequencer means for distributing samples into one or more containers within said sampler.

2. Apparatus in accordance with claim 1 in which at least one of said inner container carriers includes surfaces adapted to locate containers whereby different inner container carriers can be located within the same base with containers positioned for operation with the sampler.

3. A sampler in accordance with claim 1 further including a means for holding an inner container carrier within said base.

4. A sampler in accordance with claim 1 further including:

a cooler;

said cooler being formed as an insulator;

said insulator being adapted to receive at least one of said inner container carriers and ice and enclose the same, wherein said container carrier can be moved to and from said base together with ice as a unit.

5. A sampler comprising:

a base member;

said base member having an outer surface and an inner surface;

said inner surface having a plurality of internal configurations adapted to receive containers;

at least a first of said internal configurations being adapted to receive a first composite container for receiving a plurality of samples;

a sequencer adapted to cooperate with said base and including means for distributing samples at predetermined time intervals into said composite container;

at least a second of said internal configurations in said base member having a size and shape enabling it to receive other arrangements of containers.

6. A sampler in accordance with claim 5 in which at least one of said other arrangements of containers includes an inner container carrier adapted to hold a plurality of containers.

7. A sampler in accordance with claim 5 in which at least one of said other arrangements of containers includes a second composite container having a different volume than said first composite container.

* * * * *